US007118865B2

(12) United States Patent
Behrens et al.

(10) Patent No.: US 7,118,865 B2
(45) Date of Patent: Oct. 10, 2006

(54) METHODS FOR DIAGNOSING SEVERE SYSTEMIC LUPUS ERYTHEMATOSUS

(75) Inventors: Timothy W. Behrens, Minnetonka, MN (US); Emily C. Baechler, Minneapolis, MN (US); Peter K. Gregersen, Larchmont, NY (US)

(73) Assignees: Regents of the University of Minnesota, Minneapolis, MN (US); The Feinstein Institute for Medical Research, Manhasset, NY (US)

( * ) Notice: Subject to any disclaimer, the term of this patent is extended or adjusted under 35 U.S.C. 154(b) by 567 days.

(21) Appl. No.: 10/222,202

(22) Filed: Aug. 16, 2002

(65) Prior Publication Data

US 2004/0033498 A1 Feb. 19, 2004

(51) Int. Cl.
C12Q 1/68 (2006.01)
G01N 33/53 (2006.01)
C07H 21/02 (2006.01)
C07H 21/04 (2006.01)

(52) U.S. Cl. .................. 435/6; 435/7.1; 435/91.2; 536/23.5

(58) Field of Classification Search .............. None
See application file for complete search history.

(56) References Cited

U.S. PATENT DOCUMENTS

| 5,143,854 | A | 9/1992 | Pirrung et al. |
| 5,744,305 | A | 4/1998 | Fodor et al. |
| 2003/0148298 | A1* | 8/2003 | O'Toole et al. ............. 435/6 |
| 2004/0009479 | A1 | 1/2004 | Wohlgemuth et al. |

FOREIGN PATENT DOCUMENTS

| WO | WO 00/22093 | 4/2000 |
| WO | WO 02/57414 | 7/2002 |
| WO | WO 03/90694 | 11/2003 |

OTHER PUBLICATIONS

Liu et al. Clinical Immunology. 2004. 112: 225-230.*
Coleman et al. Drug Discovery Today. 2003. 8: 233-235.*
Balomenos et al., "Interferon-γ is Required for Lupus-like Disease and Lymphoaccumulation in MRL-*lpr* Mice," *J. Clin. Invest.*, 1998, 101(2):364-371.
Blanco et al., "Induction of Dendritic Cell Differentiation by IFN-α in Systemic Lupus Erythematosus," *Science*, 2001, 294:1540-1543.
de Veer et al., "Functional classification of interferon-stimulated genes identified using microarrays," *J. Leukocyte Biology*, 2001, 69:912-920.
Der et al., "Identification of genes differentially regulated by interferon α, β, or γ using oligonucleotide arrays," *Proc. Natl. Acad. Sci. USA*, 1998, 95:15623-15628.
Fukuyama et al., "Systemic Lupus Erythematosus After α-Interferon Therapy for Chronic Hepatitis C: A Case Report and Review of the Literature," *Am. J. Gastroenterol.*, 2000, 95:310-312.
Gu et al., "Analysis of inflammation related gene expression spectrum in ankylosing spondylitis patients using cDNA microarray," *Zhonghua Yi Xue Za Zhi*, 2001, 81(17):1030-1034 (Abstract only).
Hirano et al., "Roles of STAT3 in mediating the cell growth, differentiation and survival signals relayed through the IL-6 family of cytokine receptors," *Oncogene*, 2000, 19:2548-2556.
Hochberg, "Updating the American College of Rheumatology Revised Criteria for the Classification of Systemic Lupus Erythematosus," *Arthritis & Rheumatism*, 1997, 40(9):1725.
Jacob et al., "In Vivo Treatment of (NZB x NZW)$F_1$ Lupus-Like Nephritis with Monoclonal Antibody to γ Interferon," *J. Exp. Med.*, 1987, 166:798-803.
Rönnblom and Alm, "A Pivotal Role for the Natural Interferon α-producing Cells (Plasmacytoid Dendritic Cells) in the Pathogenesis of Lupus," *J. Exp. Med.*, 2001, 194(12):F59-F63.
Rozzo et al., "Evidence for an Interferon-Inducible Gene, *Ifi202*, in the Susceptibility to Systemic Lupus," *Immunity*, 2001, 15:435-443.
Seery et al. "Antinuclear Autoantibodies and Lupus Nephritis in Transgenic Mice Expressing Interferon γ in the Epidermis," *J. Exp. Med.*, 1997, 186(9):1451-1459.
Slide Presentation presented at *SLE: Targets for New Therapeutics—A Scientific Conference*, Salmon et al. (organizers), Jan. 10-12, 2002, Hyatt Regency Bethesda, Bethesda, Maryland.
Tan et al., "The 1982 Revised Criteria for the Classification of Systemic Lupus Erythematosus," *Arthritis and Rheumatism*, 1982, 25(11):1271-1277.

* cited by examiner

*Primary Examiner*—Carla J. Myers
(74) *Attorney, Agent, or Firm*—Fish & Richardson P.C.

(57) ABSTRACT

The invention relates to methods and materials involved in diagnosing SLE. More particularly, the invention relates to methods and materials involved in diagnosing SLE, diagnosing severe SLE, and assessing a mammal's susceptibility to develop severe SLE. For example, the invention provides nucleic acid arrays that can be used to diagnose SLE in a mammal. Such arrays can allow clinicians to diagnose SLE based on a simultaneous determination of the expression levels of many genes that are differentially expressed in SLE patients as compared to healthy controls.

6 Claims, 4 Drawing Sheets

METHODS FOR DIAGNOSING SEVERE SYSTEMIC LUPUS ERYTHEMATOSUS

STATEMENT AS TO FEDERALLY SPONSORED RESEARCH

Funding for the work described herein was provided in part by the National Institute of Arthritis and Musculoskeletal Diseases (grant no. NIH N01-AR-1-2256). The federal government thus may have certain rights in the invention.

BACKGROUND

1. Technical Field

The invention relates to methods and materials involved in diagnosing systemic lupus erythematosus (SLE). More particularly, the invention relates to methods and materials involved in diagnosing SLE, diagnosing severe SLE, and assessing a mammal's susceptibility to develop severe SLE.

2. Background Information

SLE is a chronic, inflammatory autoimmune disease characterized by the production of autoantibodies having specificity for a wide range of self-antigens. SLE autoantibodies mediate organ damage by directly binding to host tissues and by forming immune complexes that deposit in vascular tissues and activate immune cells. Organs targeted in SLE include the skin, kidneys, vasculature, joints, various blood elements, and the central nervous system (CNS). The severity of disease, the spectrum of clinical involvement, and the response to therapy vary widely among patients. This clinical heterogeneity makes it challenging to diagnose and manage lupus.

SUMMARY

The invention relates to methods and materials involved in diagnosing SLE. More particularly, the invention relates to methods and materials involved in diagnosing SLE, diagnosing severe SLE, and assessing a mammal's susceptibility to develop severe SLE. For example, the invention provides nucleic acid arrays that can be used to diagnose SLE in a mammal. Such arrays can allow clinicians to diagnose SLE based on a determination of the expression levels of many genes that are differentially expressed in SLE patients as compared to healthy controls.

In addition, the invention provides methods and materials involved in diagnosing SLE conditions that are accompanied by activation of an interferon pathway. For the purpose of this invention, the term "SLE accompanied by activation of an interferon pathway" (abbreviated "SLE-AIP") refers to any SLE condition that coexists with or is caused by activation of an interferon pathway. Activation of an interferon pathway refers to a state where interferon-regulated genes that are up-regulated in response to interferon are up-regulated and where interferon-regulated genes that are down-regulated in response to interferon are down-regulated. Typically, activation of an interferon pathway results in the presence of a gene expression profile that is similar to the gene expression profile observed in cells that were treated with interferon. An interferon pathway can be activated regardless of the presence or absence of detectable levels of interferon. For example, an SLE patient can have low levels of detectable interferon while exhibiting a gene expression profile characteristic of an activated interferon pathway. Such an SLE patient can be diagnosed as having SLE-AIP.

Diagnosing patients as having SLE-AIP can help clinicians determine appropriate treatments for those patients. For example, a clinician who diagnoses a patient as having SLE-AIP can treat that patient with medication that improves both the patient's SLE symptoms and aberrant activation of an interferon pathway. In some cases, a single medication can be used to reverse a patient's activation of an interferon pathway such that the patient's SLE symptoms are reduced or relieved. Thus, treating a patient having SLE-AIP by modulating the level of interferon pathway activation can improve that patient's health and quality of life by, for example, reducing the symptoms associated with SLE.

Typically, a diagnosis of SLE can be made on the basis of 11 criteria defined by the American College of Rheumatology (ACR). These criteria include malar rash, discoid rash, photosensitivity, oral ulcers, arthritis, serositis, renal disorder, neurologic disorder, hematologic disorder, immunologic disorder, and antinuclear antibody (Tan et al. (1982) *Arthritis Rheum.* 25:1271–1277). A mammal (e.g., a human) can be clinically diagnosed with SLE if he or she meets at least four of the eleven criteria. The term "severe SLE" as used herein refers to an SLE condition where the patient has one or more of the following: renal, central nervous system, or hematologic involvement.

The invention is based on the discovery of genes that are differentially expressed between SLE patients and healthy controls. The invention also is based on the discovery that the expression levels of these genes can be used to distinguish mammals with SLE from healthy mammals. For example, the expression levels for the genes listed in Table I can be assessed to diagnose SLE. In addition, the invention is based on the discovery that a portion of SLE patients can have SLE associated with or caused by activation of an interferon pathway. For example, SLE patients having severe SLE can be, at least partially, dependent upon the presence of an activated interferon pathway. Further, the invention is based on the discovery of genes that are differentially expressed between SLE-AIP patients and SLE patients not associated with an activated interferon pathway. For example, the expression levels for the genes listed in Table IV can be assessed to diagnose SLE-AIP.

In one aspect, the invention provides a method for diagnosing severe systemic lupus erythematosus. The method can involve determining whether or not a mammal contains cells that express at least 2 of the genes listed in Table 4 to an extent greater than or less than the average level of expression exhibited in control cells from one or more control mammals, wherein the mammal and the one or more control mammals are from the same species, and diagnosing the mammal as having severe systemic lupus erythematosus if the mammal contains the cells and diagnosing the mammal as not having severe systemic lupus erythematosus if the mammal does not contain the cells. The mammal can be a human. The control mammals can be healthy humans or humans with mild systemic lupus erythematosus. The cells and the control cells can be peripheral blood mononuclear cells. The method can involve determining whether or not the mammal contains cells that express at least 5 or at least 10 of the genes to an extent greater than or less than the level of expression exhibited in the control cells. The extent can be less than the average level of expression exhibited in control cells from at least 10 or at least 20 control mammals. The determining step can involve measuring the level of mRNA expressed from the at least 2 of the genes. In another aspect, the invention provides a method for assessing the predisposition of a mammal to develop severe systemic lupus erythematosus. The method can involve determining whether or not the mammal contains cells that express at least 2 of the genes listed in Table 4 to an extent greater than or less than the average level of expression exhibited in control cells from one or more control mammals, wherein the mammal and the one or more control mammals are from the same species, and classifying the mammal as being susceptible to develop severe systemic lupus erythematosus if the mammal contains the cells and classifying the mammal as not being susceptible to develop severe systemic lupus erythematosus if the mammal does not contain the cells. The mammal can be a human. The control mammals can be healthy humans. The cells and the control cells can be peripheral blood mononuclear cells. The method also can involve determining whether or not the mammal contains cells that express at least 5 or at least 10 of the genes to an extent greater than or less than the level of expression exhibited in the control cells. The method can involve determining whether or not the mammal contains cells that express at least 10 of the genes to an extent greater than or less than the level of expression exhibited in the control cells. The extent can be greater than or less than the average level of expression exhibited in control cells from at least 10 or at least 20 control mammals. The determining step can involve measuring the level of mRNA expressed from said at least 5 of the genes.

In another aspect, the invention provides a method for diagnosing systemic lupus erythematosus in a mammal. The method can involve determining whether or not the mammal contains cells that express at least 10 of the genes listed in Table 1 to an extent greater than or less than the average level of expression exhibited in control cells from one or more control mammals, wherein the mammal and the one or more control mammals are from the same species, and diagnosing the mammal as having systemic lupus erythematosus if the mammal contains the cells and diagnosing the mammal as not having systemic lupus erythematosus if the mammal does not contain the cells.

In yet another aspect, the invention provides a method for diagnosing systemic lupus erythematosus in a mammal. The method can involve determining whether or not the mammal contains cells that express at least 5 of the genes listed in Table 2 to an extent greater than the average level of expression exhibited in control cells from one or more control mammals, wherein the mammal and the one or more control mammals are from the same species, and diagnosing the mammal as having systemic lupus erythematosus if the mammal contains the cells and diagnosing said mammal as not having systemic lupus erythematosus if the mammal does not contain the cells.

The invention also provides a method for diagnosing systemic lupus erythematosus in a mammal. The method can involve determining whether or not the mammal contains cells that express at least 5 of the genes listed in Table 3 to an extent less than the average level of expression exhibited in control cells from one or more control mammals, wherein the mammal and the one or more control mammals are from the same species, and diagnosing the mammal as having systemic lupus erythematosus if the mammal contains the cells and diagnosing the mammal as not having systemic lupus erythematosus if the mammal does not contain the cells.

In another aspect, the invention provides a nucleic acid array containing at least 20 nucleic acid molecules. Each of the at least 20 nucleic acid molecules can have a different nucleic acid sequence, and at least 50 percent of the nucleic acid molecules of the array can contain a sequence from a gene selected from the group consisting of the genes listed in Table 1. The array can contain at least 50 nucleic acid molecules, and each of the at least 50 nucleic acid molecules can have a different nucleic acid sequence. The array can contain at least 100 nucleic acid molecules, and each of the at least 100 nucleic acid molecules can have a different nucleic acid sequence. Each of the nucleic acid molecules that contain a sequence from a gene selected from the group can contain no more than three mismatches. At least 75 percent or at least 95 percent of the nucleic acid molecules of the array can contain a sequence from a gene selected from the group. The array can contain glass.

In yet another aspect, the invention provides a nucleic acid array containing at least 5 nucleic acid molecules. Each of the at least 5 nucleic acid molecules can have a different nucleic acid sequence, and at least 50 percent of the nucleic acid molecules of the array can contain a sequence from a gene selected from the group consisting of the genes listed in Table 4. The array can contain at least 10 nucleic acid molecules, and each of the at least 10 nucleic acid molecules can have a different nucleic acid sequence. The array can contain at least 20 nucleic acid molecules, and each of the at least 20 nucleic acid molecules can have a different nucleic acid sequence. Each of the nucleic acid molecules that contain a sequence from a gene selected from the group can contain no more than three mismatches. At least 75 percent or at least 95 percent of the nucleic acid molecules of the array can contain a sequence from a gene selected from the group. The array can contain glass.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

The invention provides to methods and materials involved in diagnosing SLE. More particularly, the invention relates to methods and materials involved in diagnosing SLE, diagnosing severe SLE, and assessing a mammal's susceptibility to develop severe SLE. For example, the invention provides nucleic acid arrays that can be used to diagnose SLE, severe SLE, and/or SLE-AIP in a mammal. Such arrays can allow clinicians to diagnose SLE, severe SLE, and/or SLE-AIP based on a determination of the expression levels of many genes that are differentially expressed.

1. Diagnosing SLE

The invention provides methods for diagnosing a mammal (e.g., a human) as having SLE. In one embodiment, a mammal can be diagnosed as having SLE if it is determined that the mammal contains cells that express one or more of the genes listed in Table 1 at a level that is greater or less than the average level of expression of the same one or more genes observed in control cells obtained from control mammals. In another embodiment, a mammal can be diagnosed as having SLE if it is determined that the mammal contains cells that express one or more of the genes listed in Table 2 at a level that is greater than the average level of expression of the same one or more genes observed in control cells obtained from control mammals. In yet another embodiment, a mammal can be diagnosed as having SLE if it is determined that the mammal contains cells that express one or more of the genes listed in Table 3 at a level that is less than the average level of expression of the same one or more genes observed in control cells obtained from control mammals.

The mammal can be any mammal such as a human, dog, mouse, or rat. Any cell type can be isolated and evaluated. For example, peripheral blood mononuclear cells (PMBC), total white blood cells, lymph node cells, spleen cells, or tonsil cells can be isolated from a human patient and evaluated to determine if that patient contains cells that (1) express one or more of the genes listed in Table 1 at a level that is greater or less than the average level of expression observed in control cells, (2) express one or more of the genes listed in Table 2 at a level that is greater than the average level of expression observed in control cells, or (3) express one or more of the genes listed in Table 3 at a level that is less than the average level of expression observed in control cells. The expression of any number of the genes listed in Tables 1, 2, or 3 can be evaluated to diagnose SLE. For example, the expression of one or more than one (e.g., two, three, four, five, six, seven, eight, nine, ten, 15, 20, 25, 30, or more than 30) of the genes listed in Table 1, 2, or 3 can be used.

The expression level can be greater than or less than the average level observed in control cells obtained from control mammals. Typically, a gene can be classified as being expressed at a level that is greater than or less than the average level observed in control cells if the expression levels differ by at least 1-fold (e.g., 1.5-fold, 2-fold, 3-fold, or more than 3-fold). In addition, the control cells typically are the same type of cells as those isolated from the mammal being evaluated. In some cases, the control cells can be isolated from one or more mammals that are from the same species as the mammal being evaluated. When diagnosing SLE, the control cells can be isolated from healthy mammals such as healthy humans who do not have SLE. Any number of control mammals can be used to obtain the control cells. For example, control cells can be obtained from one or more healthy mammals (e.g., at least 5, at least 10, at least 15, at least 20, or more than 20 control mammals).

Any method can be used to determine whether or not a specific gene is expressed at a level that is greater or less than the average level of expression observed in control cells. For example, the level of expression from a particular gene can be measured by assessing the level of mRNA expression from the gene. Levels of mRNA expression can be evaluated using, without limitation, northern blotting, slot blotting, quantitative reverse transcriptase polymerase chain reaction (RT-PCR), or chip hybridization techniques. Methods for chip hybridization assays include, without limitation, those described herein. Such methods can be used to determine simultaneously the relative expression levels of multiple mRNAs. Alternatively, the level of expression from a particular gene can be measured by assessing polypeptide levels. Polypeptide levels can be measured using any method such as immuno-based assays (e.g., ELISA), western blotting, or silver staining.

TABLE 1

Genes with expression levels that differ between SLE patients and normal controls

| Accession No. | Gene |
|---|---|
| U60060 | fasciculation and elongation protein zeta 1 (zygin I) |
| AF057036 | collagen-like tail subunit (single strand of homotrimer) of asymmetric acetylcholinesterase |
| M93107 | 3-hydroxybutyrate dehydrogenase (heart, mitochondrial) |
| U14575 | protein phosphatase 1, regulatory (inhibitor) subunit 8 |
| X15882 | collagen VI alpha-2 C-terminal globular domain |
| S68805 | glycine amidinotransferase (L-arginine:glycine amidinotransferase) |
| U75744 | deoxyribonuclease I-like 3 |
| AF091071 | similar to S. cerevisiae RER1 |
| AI651806 | cysteine-rich motor neuron 1 |
| AB028994 | KIAA1071 protein |
| S75168 | megakaryocyte-associated tyrosine kinase |
| X73617 | T cell receptor delta locus |
| X07730 | kallikrein 3, (prostate specific antigen) |
| AF009787 | T cell receptor beta locus |
| M21624 | T cell receptor delta locus |
| AB009598 | beta-1,3-glucuronyltransferase 3 (glucuronosyltransferase I) |
| AL021154 | E2F transcription factor 2 |
| L25444 | TAF6 RNA polymerase II, TATA box binding protein (TBP)-associated factor, 80 kD |
| AJ001383 | lymphocyte antigen 94 homolog, activating NK-receptor; NK-p46, (mouse) |
| U75370 | polymerase (RNA) mitochondrial (DNA directed) |
| AL049365 | DKFZp586A0618 |
| M16801 | nuclear receptor subfamily 3, group C, member 2 |
| M28827 | CD1C antigen, c polypeptide |
| U51712 | hypothetical protein SMAP31 |
| X66079 | Spi-B transcription factor (Spi-1/PU.1 related) |
| U11276 | killer cell lectin-like receptor subfamily B, member 1 |
| M36881 | lymphocyte-specific protein tyrosine kinase |
| M31523 | transcription factor 3 (E2A immunoglobulin enhancer binding factors E12/E47) |
| M26062 | interleukin 2 receptor, beta |
| AF026031 | putative mitochondrial outer membrane protein import receptor |
| AB011115 | KIAA0543 protein |
| AF041261 | leukocyte immunoglobulin-like receptor, subfamily A (without TM domain), member 4 |
| D55716 | MCM7 minichromosome maintenance deficient 7 (S. cerevisiae) |
| L04282 | zinc finger protein 148 (pHZ-52) |
| AJ001687 | DNA segment on chromosome 12 (unique) 2489 expressed sequence |
| AI524873 | like mouse brain protein E46 |
| U76421 | adenosine deaminase, RNA-specific, B1 (homolog of rat RED1) |
| AF031137 | lymphocyte antigen 117 |
| X59871 | transcription factor 7 (T-cell specific, HMG-box) |
| U43408 | tyrosine kinase, non-receptor, 1 |
| AB018289 | KIAA0746 protein |
| AI761647 | IMAGE-2370113 |
| M18737 | granzyme A (granzyme 1, cytotoxic T-lymphocyte-associated serine esterase 3) |
| AB023220 | ubiquitin specific protease 20 |

TABLE 1-continued

Genes with expression levels that differ between SLE patients and normal controls

| Accession No. | Gene |
|---|---|
| W26633 | melanoma antigen, family D, 1 |
| M68892 | integrin, beta 7 |
| AJ236885 | zinc finger protein 148 (pHZ-52) |
| L13858 | son of sevenless (Drosophilia) homolog 2 |
| AF094481 | CGG triplet repeat binding protein 1 |
| M28215 | RAB5A, member RAS oncogene family |
| U43083 | guanine nucleotide binding protein (G protein), q polypeptide |
| X02344 | tubulin, beta, 2 |
| M22324 | alanyl (membrane) aminopeptidase (aminopeptidase N, aminopeptidase M, microsomal aminopeptidase, CD13, p150) |
| Y07566 | Ric-like, expressed in many tissues (Drosophila) |
| U50553 | DEAD/H (Asp-Glu-Ala-Asp/His) box polypeptide 3 |
| X54134 | protein tyrosine phosphatase, receptor type, E |
| L40388 | thyroid receptor interacting protein 15 |
| L19872 | aryl hydrocarbon receptor |
| U78107 | N-ethylmaleimide-sensitive factor attachment protein, gamma |
| AL050272 | DKFZP566B183 protein |
| U56998 | cytokine-inducible kinase |
| AI189226 | RAB31, member RAS oncogene family |
| Z50781 | delta sleep inducing peptide, immunoreactor |
| S87759 | protein phosphatase 1A (formerly 2C), magnesium-dependent, alpha isoform |
| U88629 | ELL-RELATED RNA POLYMERASE II, ELONGATION FACTOR |
| AF006513 | chromodomain helicase DNA binding protein 1 |
| AI138605 | hypothetical protein DKFZp566A1524 |
| L16794 | MADS box transcription enhancer factor 2, polypeptide D (myocyte enhancer factor 2D) |
| AL080235 | Ras-induced senescence 1 |
| L17418 | complement component (3b/4b) receptor 1, including Knops blood group system |
| Y00816 | complement component (3b/4b) receptor 1, including Knops blood group system |
| M63835 | Fc fragment of IgG, high affinity Ia, receptor for (CD64) |
| L13943 | glycerol kinase |
| U89278 | early development regulator 2 (homolog of polyhomeotic 2) |
| U58334 | tumor protein p53 binding protein, 2 |
| X54134 | protein tyrosine phosphatase, receptor type, E |
| X59834 | glutamate-ammonia ligase (glutamine synthase) |
| AL047596 | capicua homolog (Drosophila) |
| AB023211 | peptidyl arginine deiminase, type II |
| D43945 | transcription factor EC |
| U79273 | clone 23933 |
| Z18956 | solute carrier family 6 (neurotransmitter transporter, taurine), member 6 |
| Y10313 | interferon-related developmental regulator 1 |
| AF004849 | homeodomain interacting protein kinase 3 |
| AI808958 | KIAA0870 protein |
| U47634 | tubulin, beta, 4 |
| X55988 | ribonuclease, RNase A family, 2 (liver, eosinophil-derived neurotoxin) |
| W29030 | CGI-49 protein |
| U12471 | thrombospondin-1 |
| AF013591 | sudD (suppressor of bimD6, Aspergillus nidulans) homolog |
| X52015 | interleukin 1 receptor antagonist |
| M16967 | coagulation factor V (proaccelerin, labile factor) |
| U57094 | RAB27A, member RAS oncogene family |
| U66711 | lymphocyte antigen 6 complex, locus E |
| AA521060 | IMAGE-826408 |
| X68090 | IgG Fc receptor class IIA |
| Y08136 | acid sphingomyelinase-like phosphodiesterase |
| AL049685 | hypothetical protein similar to small G proteins, especially RAP-2A |
| L28957 | phosphate cytidylyltransferase 1, choline, alpha isoform |
| Z22576 | CD69 antigen (p60, early T-cell activation antigen) |
| U41766 | a disintegrin and metalloproteinase domain 9 (meltrin gamma) |
| M57230 | interleukin 6 signal transducer (gp130, oncostatin M receptor) |
| X17094 | paired basic amino acid cleaving enzyme (furin, membrane associated receptor protein) |
| AC005192 | interferon-related developmental regulator 1 |
| AI547258 | metallothionein 2A |
| L22075 | guanine nucleotide binding protein (G protein), alpha 13 |
| U22431 | hypoxia-inducible factor 1, alpha subunit (basic helix-loop-helix transcription factor) |
| AB006746 | phospholipid scramblase 1 |
| AF030196 | stannin |
| AA010078 | H4 histone family, member D |
| X56807 | desmocollin 2 |
| AL080156 | DKFZP434J214 protein |
| AF017257 | v-ets erythroblastosis virus E26 oncogene homolog 2 (avian) |
| AL049340 | DKFZp564P056 |
| M24283 | intercellular adhesion molecule 1 (CD54), human rhinovirus receptor |
| D49817 | 6-phosphofructo-2-kinase/fructose-2,6-biphosphatase 3 |
| AF016903 | agrin |
| U77914 | jagged 1 (Alagille syndrome) |
| M33882 | myxovirus (influenza) resistance 1, homolog of murine (interferon-inducible protein p78) |
| U68385 | Meis1, myeloid ecotropic viral integration site 1 homolog 3 (mouse) |
| L05515 | cAMP response element-binding protein CRE-BPa |
| U15555 | serine palmitoyltransferase, long chain base subunit 2 |
| L42025 | HIV-1 Rev binding protein |
| X07834 | superoxide dismutase 2, mitochondrial |
| D90144 | small inducible cytokine A3 |
| M13755 | interferon-stimulated protein, 15 kDa |
| M83670 | carbonic anhydrase IV |
| M55047 | synaptotagmin I |
| U91512 | ninjurin 1 |
| AB008775 | aquaporin 9 |
| X79535 | tubulin, beta polypeptide |
| J04102 | v-ets erythroblastosis virus E26 oncogene homolog 2 (avian) |
| D10040 | fatty-acid-Coenzyme A ligase, long-chain 2 |
| AW044649 | sin3-associated polypeptide, 30 kD |
| X03473 | H1 histone family, member 0 |
| AB007448 | solute carrier family 22 (organic cation transporter), member 4 |
| Z14138 | mitogen-activated protein kinase kinase kinase 8 |
| X02419 | uPA |
| U10473 | UDP-Gal:betaGlcNAc beta 1,4-galactosyltransferase, polypeptide 1 |
| AI679353 | solute carrier family 11 (proton-coupled divalent metal ion transporters), member 1 |
| AA203213 | interferon-stimulated protein, 15 kDa |
| AB018259 | KIAA0716 gene product |
| AF055993 | sin3-associated polypeptide, 30 kD |
| X54486 | serine (or cysteine) proteinase inhibitor, clade G (C1 inhibitor), member 1 |
| AJ225089 | 2'-5'-oligoadenylate synthetase-like |
| AL022318 | similar to APOBEC1 |
| S59049 | regulator of G-protein signalling 1 |
| Y10032 | serum/glucocorticoid regulated kinase |
| AI924594 | tetraspan 2 |
| D21205 | zinc finger protein 147 (estrogen-responsive finger protein) |
| U37707 | membrane protein, palmitoylated 3 (MAGUK p55 subfamily member 3) |
| L40387 | 2'-5'-oligoadenylate synthetase-like |
| X78711 | glycerol kinase |
| D10923 | putative chemokine receptor; GTP-binding protein |
| AW006742 | IMAGE-2489058 |
| AL109730 | EUROIMAGE 68600 |
| X99699 | XIAP associated factor-1 |
| AB000115 | hypothetical protein, expressed in osteoblast |
| L13210 | lectin, galactoside-binding, soluble, 3 binding protein |
| U22970 | interferon, alpha-inducible protein (clone IFI-6-16) |
| U96721 | Hermansky-Pudlak syndrome |
| L10126 | activin A receptor, type IB |
| S62138 | TLS/CHOP |

TABLE 1-continued

Genes with expression levels that differ between SLE patients and normal controls

| Accession No. | Gene |
|---|---|
| M33684 | protein tyrosine phosphatase, non-receptor type 1 |
| M63978 | vascular endothelial growth factor |
| X89101 | tumor necrosis factor receptor superfamily, member 6 |
| M60278 | diphtheria toxin receptor (heparin-binding epidermal growth factor-like growth factor) |
| X59770 | interleukin 1 receptor, type II |
| X04500 | interleukin 1, beta |
| D30783 | epiregulin |
| U43774 | Fc fragment of IgA, receptor for |

TABLE 2

Genes from Table 1 that are higher in SLE patients as compared to controls

| Accession No. | Gene |
|---|---|
| L13858 | son of sevenless (Drosophilia) homolog 2 |
| AF094481 | CGG triplet repeat binding protein 1 |
| M28215 | RAB5A, member RAS oncogene family |
| U43083 | guanine nucleotide binding protein (G protein), q polypeptide |
| X02344 | tubulin, beta, 2 |
| M22324 | alanyl (membrane) aminopeptidase (aminopeptidase N, aminopeptidase M, microsomal aminopeptidase, CD13, p150) |
| Y07566 | Ric-like, expressed in many tissues (Drosophila) |
| U50553 | DEAD/H (Asp-Glu-Ala-Asp/His) box polypeptide 3 |
| X54134 | protein tyrosine phosphatase, receptor type, E |
| L40388 | thyroid receptor interacting protein 15 |
| L19872 | aryl hydrocarbon receptor |
| U78107 | N-ethylmaleimide-sensitive factor attachment protein, gamma |
| AL050272 | DKFZP566B183 protein |
| U56998 | cytokine-inducible kinase |
| AI189226 | RAB31, member RAS oncogene family |
| Z50781 | delta sleep inducing peptide, immunoreactor |
| S87759 | protein phosphatase 1A (formerly 2C), magnesium-dependent, alpha isoform |
| U88629 | ELL-RELATED RNA POLYMERASE II, ELONGATION FACTOR |
| AF006513 | chromodomain helicase DNA binding protein 1 |
| AI138605 | hypothetical protein DKFZp566A1524 |
| L16794 | MADS box transcription enhancer factor 2, polypeptide D (myocyte enhancer factor 2D) |
| AL080235 | Ras-induced senescence 1 |
| L17418 | complement component (3b/4b) receptor 1, including Knops blood group system |
| Y00816 | complement component (3b/4b) receptor 1, including Knops blood group system |
| M63835 | Fc fragment of IgG, high affinity Ia, receptor for (CD64) |
| L13943 | glycerol kinase |
| U89278 | early development regulator 2 (homolog of polyhomeotic 2) |
| U58334 | tumor protein p53 binding protein, 2 |
| X54134 | protein tyrosine phosphatase, receptor type, E |
| X59834 | glutamate-ammonia ligase (glutamine synthase) |
| AL047596 | capicua homolog (Drosophila) |
| AB023211 | peptidyl arginine deiminase, type II |
| D43945 | transcription factor EC |
| U79273 | clone 23933 |
| Z18956 | solute carrier family 6 (neurotransmitter transporter, taurine), member 6 |
| Y10313 | interferon-related developmental regulator 1 |
| AF004849 | homeodomain interacting protein kinase 3 |
| AI808958 | KIAA0870 protein |
| U47634 | tubulin, beta, 4 |
| X55988 | ribonuclease, RNase A family, 2 (liver, eosinophil-derived neurotoxin) |
| W29030 | CGI-49 protein |
| U12471 | thrombospondin-1 |

TABLE 2-continued

Genes from Table 1 that are higher in SLE patients as compared to controls

| Accession No. | Gene |
|---|---|
| AF013591 | sudD (suppressor of bimD6, Aspergillus nidulans) homolog |
| X52015 | interleukin 1 receptor antagonist |
| M16967 | coagulation factor V (proaccelerin, labile factor) |
| U57094 | RAB27A, member RAS oncogene family |
| U66711 | lymphocyte antigen 6 complex, locus E |
| AA521060 | IMAGE-826408 |
| X68090 | IgG Fc receptor class IIA |
| Y08136 | acid sphingomyelinase-like phosphodiesterase |
| AL049685 | hypothetical protein similar to small G proteins, especially RAP-2A |
| L28957 | phosphate cytidylyltransferase 1, choline, alpha isoform |
| Z22576 | CD69 antigen (p60, early T-cell activation antigen) |
| U41766 | a disintegrin and metalloproteinase domain 9 (meltrin gamma) |
| M57230 | interleukin 6 signal transducer (gp 130, oncostatin M receptor) |
| X17094 | paired basic amino acid cleaving enzyme (furin, membrane associated receptor protein) |
| AC005192 | interferon-related developmental regulator 1 |
| AI547258 | metallothionein 2A |
| L22075 | guanine nucleotide binding protein (G protein), alpha 13 |
| U22431 | hypoxia-inducible factor 1, alpha subunit (basic helix-loop-helix transcription factor) |
| AB006746 | phospholipid scramblase 1 |
| AF030196 | stannin |
| AA010078 | H4 histone family, member D |
| X56807 | desmocollin 2 |
| AL080156 | DKFZP434J214 protein |
| AF017257 | v-ets erythroblastosis virus E26 oncogene homolog 2 (avian) |
| AL049340 | DKFZp564P056 |
| M24283 | intercellular adhesion molecule 1 (CD54), human rhinovirus receptor |
| D49817 | 6-phosphofructo-2-kinase/fructose-2,6-biphosphatase 3 |
| AF016903 | agrin |
| U77914 | jagged 1 (Alagille syndrome) |
| M33882 | myxovirus (influenza) resistance 1, homolog of murine (interferon-inducible protein p78) |
| U68385 | Meis1, myeloid ecotropic viral integration site 1 homolog 3 (mouse) |
| L05515 | cAMP response element-binding protein CRE-BPa |
| U15555 | serine palmitoyltransferase, long chain base subunit 2 |
| L42025 | HIV-1 Rev binding protein |
| X07834 | superoxide dismutase 2, mitochondrial |
| D90144 | small inducible cytokine A3 |
| M13755 | interferon-stimulated protein, 15 kDa |
| M83670 | carbonic anhydrase IV |
| M55047 | synaptotagmin I |
| U91512 | ninjurin 1 |
| AB008775 | aquaporin 9 |
| X79535 | tubulin, beta polypeptide |
| J04102 | v-ets erythroblastosis virus E26 oncogene homolog 2 (avian) |
| D10040 | fatty-acid-Coenzyme A ligase, long-chain 2 |
| AW044649 | sin3-associated polypeptide, 30 kD |
| X03473 | H1 histone family, member 0 |
| AB007448 | solute carrier family 22 (organic cation transporter), member 4 |
| Z14138 | mitogen-activated protein kinase kinase kinase 8 |
| X02419 | uPA |
| U10473 | UDP-Gal:betaGlcNAc beta 1,4-galactosyltransferase, polypeptide 1 |
| AI679353 | solute carrier family 11 (proton-coupled divalent metal ion transporters), member 1 |
| AA203213 | interferon-stimulated protein, 15 kDa |
| AB018259 | KIAA0716 gene product |
| AF055993 | sin3-associated polypeptide, 30 kD |
| X54486 | serine (or cysteine) proteinase inhibitor, clade G (C1 inhibitor), member 1 |
| AJ225089 | 2'-5'-oligoadenylate synthetase-like |
| AL022318 | similar to APOBEC1 |
| S59049 | regulator of G-protein signalling 1 |
| Y10032 | serum/glucocorticoid regulated kinase |

TABLE 2-continued

Genes from Table 1 that are higher in
SLE patients as compared to controls

| Accession No. | Gene |
| --- | --- |
| AI924594 | tetraspan 2 |
| D21205 | zinc finger protein 147 (estrogen-responsive finger protein) |
| U37707 | membrane protein, palmitoylated 3 (MAGUK p55 subfamily member 3) |
| L40387 | 2'-5'-oligoadenylate synthetase-like |
| X78711 | glycerol kinase |
| D10923 | putative chemokine receptor; GTP-binding protein |
| AW006742 | IMAGE-2489058 |
| AL109730 | EUROIMAGE 68600 |
| X99699 | XIAP associated factor-1 |
| AB000115 | hypothetical protein, expressed in osteoblast |
| L13210 | lectin, galactoside-binding, soluble, 3 binding protein |
| U22970 | interferon, alpha-inducible protein (clone IFI-6-16) |
| U96721 | Hermansky-Pudlak syndrome |
| L10126 | activin A receptor, type IB |
| S62138 | TLS/CHOP |
| M33684 | protein tyrosine phosphatase, non-receptor type 1 |
| M63978 | vascular endothehal growth factor |
| X89101 | tumor necrosis factor receptor superfamily, member 6 |
| M60278 | diphtheria toxin receptor (heparin-binding epidermal growth factor-like growth factor) |
| X59770 | interleukin 1 receptor, type II |
| X04500 | interleukin 1, beta |
| D30783 | epiregulin |
| U43774 | Fc fragment of IgA, receptor for |

TABLE 3

Genes from Table 1 that are lower in
SLE patients as compared to controls

| Accession No. | Gene |
| --- | --- |
| U60060 | fasciculation and elongation protein zeta 1 (zygin I) |
| AF057036 | collagen-like tail subunit (single strand of homotrimer) of asymmetric acetylcholinesterase |
| M93107 | 3-hydroxybutyrate dehydrogenase (heart, mitochondrial) |
| U14575 | protein phosphatase 1, regulatory (inhibitor) subunit 8 |
| X15882 | collagen VI alpha-2 C-terminal globular domain |
| S68805 | glycine amidinotransferase (L-arginine:glycine amidinotransferase) |
| U75744 | deoxyribonuclease I-like 3 |
| AF091071 | similar to S. cerevisiae RER1 |
| AI651806 | cysteine-rich motor neuron 1 |
| AB028994 | KIAA1071 protein |
| S75168 | megakaryocyte-associated tyrosine kinase |
| X73617 | T cell receptor delta locus |
| X07730 | kallikrein 3, (prostate specific antigen) |
| AF009787 | T cell receptor beta locus |
| M21624 | T cell receptor delta locus |
| AB009598 | beta-1,3-glucuronyltransferase 3 (glucuronosyltransferase I) |
| AL021154 | E2F transcription factor 2 |
| L25444 | TAF6 RNA polymerase II, TATA box binding protein (TBP)-associated factor, 80 kD |
| AJ001383 | lymphocyte antigen 94 homolog, activating NK-receptor; NK-p46, (mouse) |
| U75370 | polymerase (RNA) mitochondrial (DNA directed) |
| AL049365 | DKFZp586A0618 |
| M16801 | nuclear receptor subfamily 3, group C, member 2 |
| M28827 | CD1C antigen, c polypeptide |
| U51712 | hypothetical protein SMAP31 |
| X66079 | Spi-B transcription factor (Spi-1/PU.1 related) |
| U11276 | killer cell lectin-like receptor subfamily B, member 1 |
| M36881 | lymphocyte-specific protein tyrosine kinase |
| M31523 | transcription factor 3 (E2A immunoglobulin enhancer binding factors E12/E47) |
| M26062 | interleukin 2 receptor, beta |
| AF026031 | putative mitochondrial outer membrane protein import receptor |

TABLE 3-continued

Genes from Table 1 that are lower in
SLE patients as compared to controls

| Accession No. | Gene |
| --- | --- |
| AB011115 | KIAA0543 protein |
| AF041261 | leukocyte immunoglobulin-like receptor, subfamily A (without TM domain), member 4 |
| D55716 | MCM7 minichromosome maintenance deficient 7 (S. cerevisiae) |
| L04282 | zinc finger protein 148 (pHZ-52) |
| AJ001687 | DNA segment on chromosome 12 (unique) 2489 expressed sequence |
| AI524873 | like mouse brain protein E46 |
| U76421 | adenosine deaminase, RNA-specific, B1 (homolog of rat RED1) |
| AF031137 | lymphocyte antigen 117 |
| X59871 | transcription factor 7 (T-cell specific, HMG-box) |
| U43408 | tyrosine kinase, non-receptor, 1 |
| AB018289 | KIAA0746 protein |
| AI761647 | IMAGE-2370113 |
| M18737 | granzyme A (granzyme 1, cytotoxic T-lymphocyte-associated serine esterase 3) |
| AB023220 | ubiquitin specific protease 20 |
| W26633 | melanoma antigen, family D, 1 |
| M68892 | integrin, beta 7 |
| AJ236885 | zinc finger protein 148 (pHZ-52) |

2. Diagnosing Severe SLE and SLE-AIP

The invention also provides methods for diagnosing a mammal (e.g., a human) as having severe SLE or SLE-AIP. In one embodiment, a mammal can be diagnosed as having severe SLE or SLE-AIP if it is determined that the mammal contains cells that express one or more of the genes listed in Table 4 at a level that is greater than the average level of expression of the same one or more genes observed in control cells obtained from control mammals.

As described above, the mammal can be any mammal such as a human, dog, mouse, or rat. Any cell type can be isolated and evaluated. For example, peripheral blood mononuclear cells (PMBC), total white blood cells, lymph node cells, spleen cells, or tonsil cells can be isolated from a human patient and evaluated to determine if that patient contains cells that express one or more of the genes listed in Table 4 at a level that is greater than the average level of expression observed in control cells. The expression of any number of the genes listed in Table 4 can be evaluated to diagnose severe SLE or SLE-AIP. For example, the expression of one or more than one (e.g., two, three, four, five, six, seven, eight, nine, ten, 11, 12, 13, or all 14) of the genes listed in Table 4 can be used.

The expression level can be greater than or less than the average level observed in control cells obtained from control mammals. Typically, a gene can be classified as being expressed at a level that is greater than or less than the average level observed in control cells if the expression levels differ by at least 1-fold (e.g., 1.5-fold, 2-fold, 3-fold, or more than 3-fold). In addition, the control cells typically are the same type of cells as those isolated from the mammal being evaluated. In some cases, the control cells can be isolated from one or more mammals that are from the same species as the mammal being evaluated. When diagnosing severe SLE or SLE-AIP, the control cells can be isolated from mammals having mild SLE or from healthy mammals such as healthy humans who do not have SLE. Any number of control mammals can be used to obtain the control cells. For example, control cells can be obtained from one or more healthy mammals (e.g., at least 5, at least 10, at least 15, at least 20, or more than 20 control mammals).

Any method can be used to determine whether or not a specific gene is expressed at a level that is greater or less than the average level of expression observed in control cells. For example, the level of expression from a particular gene can be measured by assessing the level of mRNA expression from the gene. Levels of mRNA expression can be evaluated using, without limitation, northern blotting, slot blotting, quantitative reverse transcriptase polymerase chain reaction (RT-PCR), or chip hybridization techniques. Methods for chip hybridization assays include, without limitation, those described herein. Such methods can be used to determine simultaneously the relative expression levels of multiple mRNAs. Alternatively, the level of expression from a particular gene can be measured by assessing polypeptide levels. Polypeptide levels can be measured using any method such as immuno-based assays (e.g., ELISA), western blotting, or silver staining.

TABLE 4

Genes with expression levels that difer between SLE patients having low and high IFN scores

| Accession No. | Gene |
|---|---|
| M63835 | Fc fragment of IgG, high affinity Ia, receptor for (CD64) |
| X54486 | serine (or cysteine) proteinase inhibitor, clade G (C1 inhibitor), member 1 |
| L13210 | lectin, galactoside-binding, soluble, 3 binding protein |
| M33882 | myxovirus (influenza) resistance 1, homolog of murine (interferon-inducible protein p78) |
| AA203213 | interferon-stimulated protein, 15 kDa |
| X99699 | XIAP assoeiated factor-1 |
| AJ225089 | 2'-5'-oligoadenylate synthetase-like |
| U22970 | interferon, alpha-inducible protein (clone IFI-6-16) |
| AB000115 | hypothetical protein, expressed in osteoblast |
| AL047596 | capicua homolog (Drosophila) |
| AB006746 | phospholipid scramblase 1 |
| AL022318 | similar to APOBEC1 |
| U66711 | lymphocyte antigen 6 complex, locus E |
| X55988 | ribonuclease, RNase A family, 2 (liver, eosinophil-derived neurotoxin) |

3. Identifying Mammals Predisposed to Develop Severe SLE and SLE-AIP

The invention also provides methods for diagnosing a mammal (e.g., a human) as being predisposed to develop severe SLE or SLE-AIP. In one embodiment, a mammal can be diagnosed as being predisposed to develop severe SLE or SLE-AIP if it is determined that the mammal contains cells that express one or more of the genes listed in Table 4 at a level that is greater than the average level of expression of the same one or more genes observed in control cells obtained from control mammals.

As described above, the mammal can be any mammal such as a human, dog, mouse, or rat. Any cell type can be isolated and evaluated. For example, peripheral blood mononuclear cells (PMBC), total white blood cells, lymph node cells, spleen cells, or tonsil cells can be isolated from a human patient and evaluated to determine if that patient contains cells that express one or more of the genes listed in Table 4 at a level that is greater than the average level of expression observed in control cells. The expression of any number of the genes listed in Table 4 can be evaluated to diagnose a mammal as being predisposed to develop severe SLE or SLE-AIP. For example, the expression of one or more than one (e.g., two, three, four, five, six, seven, eight, nine, ten, 11, 12, 13, or all 14) of the genes listed in Table 4 can be used.

The expression level can be greater than or less than the average level observed in control cells obtained from control mammals. Typically, a gene can be classified as being expressed at a level that is greater than or less than the average level observed in control cells if the expression levels differ by at least 1-fold (e.g., 1.5-fold, 2-fold, 3-fold, or more than 3-fold). In addition, the control cells typically are the same type of cells as those isolated from the mammal being evaluated. In some cases, the control cells can be isolated from one or more mammals that are from the same species as the mammal being evaluated. When determining a mammal's susceptibility to develop severe SLE or SLE-AIP, the control cells can be isolated from mammals having mild SLE or from healthy mammals such as healthy humans who do not have SLE. Any number of control mammals can be used to obtain the control cells. For example, control cells can be obtained from one or more healthy mammals (e.g., at least 5, at least 10, at least 15, at least 20, or more than 20 control mammals).

Any method can be used to determine whether or not a specific gene is expressed at a level that is greater or less than the average level of expression observed in control cells. For example, the level of expression from a particular gene can be measured by assessing the level of mRNA expression from the gene. Levels of mRNA expression can be evaluated using, without limitation, northern blotting, slot blotting, quantitative reverse transcriptase polymerase chain reaction (RT-PCR), or chip hybridization techniques. Methods for chip hybridization assays include, without limitation, those described herein. Such methods can be used to determine simultaneously the relative expression levels of multiple mRNAs. Alternatively, the level of expression from a particular gene can be measured by assessing polypeptide levels. Polypeptide levels can be measured using any method such as immuno-based assays (e.g., ELISA), western blotting, or silver staining.

4. Arrays

The invention also provides nucleic acid arrays. The arrays provided herein can be two-dimensional arrays, and can contain at least 10 different nucleic acid molecules (e.g., at least 20, at least 30, at least 50, at least 100, or at least 200 different nucleic acid molecules). Each nucleic acid molecule can have any length. For example, each nucleic acid molecule can be between 10 and 250 nucleotides (e.g., between 12 and 200, 14 and 175, 15 and 150, 16 and 125, 18 and 100, 20 and 75, or 25 and 50 nucleotides) in length. In addition, each nucleic acid molecule can have any sequence. For example, the nucleic acid molecules of the arrays provided herein can contain sequences that are present within the genes listed in Tables 1, 2, 3, and/or 4.

Typically, at least 25% (e.g., at least 30%, at least 40%, at least 50%, at least 60%, at least 75%, at least 80%, at least 90%, at least 95%, or 100%) of the nucleic acid molecules of an array provided herein contain a sequence that is (1) at least 10 nucleotides (e.g., at least 11, 12, 13, 14, 15, 16, 17, 18, 19, 20, 25, or more nucleotides) in length and (2) at least about 95 percent (e.g., at least about 96, 97, 98, 99, or 100) percent identical, over that length, to a sequence present within a gene listed in Tables 1, 2, 3, and/or 4. For example, an array can contain 100 nucleic acid molecules located in known positions, where each of the 100 nucleic acid molecules is 100 nucleotides in length while containing a sequence that is (1) 30 nucleotides is length, and (2) 100 percent identical, over that 30 nucleotide length, to a sequence of one of the genes listed in Table 4. Thus, a nucleic acid molecule of an array provided herein can contain a sequence present within a gene listed in Tables 1, 2, 3, and/or 4, where that sequence contains one or more (e.g., one, two, three, four, or more) mismatches.

The nucleic acid arrays provided herein can contain nucleic acid molecules attached to any suitable surface (e.g., plastic or glass). In addition, any method can be use to make a nucleic acid array. For example, spotting techniques and in situ synthesis techniques can be used to make nucleic acid arrays. Further, the methods disclosed in U.S. Pat. Nos. 5,744,305 and 5,143,854 can be used to make nucleic acid arrays.

The invention will be further described in the following examples, which do not limit the scope of the invention described in the claims.

EXAMPLES

Example 1

Identifying Genes that Can be Used to Diagnose SLE

PBMCs were collected from 48 SLE patients and 42 healthy, age- and gender-matched control individuals. All patients had physician-verified SLE and met at least four of the eleven ACR criteria for lupus. The average age of SLE patients was 45±11 years, and the average age of controls was 34±13 years. Each PBMC sample contained monocytes/macrophages, B and T lymphocytes, and natural killer cells.

For the first 11 patients and 11 controls, poly $A^+$ mRNA was extracted from the collected PBMC samples. Briefly, 60 mL of peripheral blood was drawn into a heparinized syringe. Whole blood was layered over an equal volume of Histopaque and centrifuged at 400×g for 30 minutes at 25° C. Plasma was harvested and stored at −80° C. PBMCs were harvested and washed twice in 1×PBS, and the mRNA was isolated using a FastTrack mRNA isolation kit (Invitrogen, Carlsbad, Calif.).

For the next 37 patients and 31 controls, total RNA was extracted from the collected PBMC samples. Briefly, peripheral blood was drawn into CPT tubes (Becton-Dickinson, Franklin Lakes, N.J.), and plasma and PBMCs were collected according to manufacturer's protocol. Plasma was stored at −80° C., and total RNA was isolated from PBMCs using Trizol (Gibco-BRL, Invitrogen, Carlsbad, Calif.) followed by an RNeasy cleanup (Qiagen, Valencia, Calif.).

About 5 to 10 μg of total RNA or about 100–200 ng of poly $A^+$ RNA was used to prepare biotinylated cRNA for hybridization using the standard Affymetrix protocol (Expression Analysis Technical Manual, Affymetrix, Inc., 2000). Briefly, RNA was converted to first strand cDNA using a T7-linked oligo(dT) primer (Genset, La Jolla, Calif.) followed by second strand synthesis (Gibco-BRL). The dscDNA was then used as template for labeled in vitro transcription reactions using biotinylated ribonucleotides (Enzo, Farmingdale, N.Y.). Fifteen μg of each labeled cRNA was hybridized to Affymetrix U95A GeneChips (Affymetrix, Santa Clara, Calif.) using standard conditions in an Affymetrix fluidics station.

After chip hybridization and initial data analysis, the expression values for 10,260 genes represented on the chip were compared between SLE patients and controls using a non-paired Student's T-test.

Affymetrix Microarray Suite (MAS) 4.0 software was used to generate expression values (referred to as an "average difference;" AD) for each gene. Each chip was scaled to an overall intensity of 1500 to correct for minor differences in overall chip hybridization intensity and to allow comparison between chips. A threshold of 20 AD units was assigned to any gene that was called "Absent" by MAS. In addition, any gene with an AD less than 20 was assigned this threshold. Data from U95Avl and U95Av2 chips were aligned by discarding the 51 probe sets that were not present on both chips. The analysis identified 161 unique genes that were differentially expressed using the following criteria: $p<0.001$, fold-change>1.5, mean expression value difference>100 units.

Despite the use of the same oligo(dT) primer for cDNA synthesis, consistent differences between the raw AD values obtained from polyA$^+$ RNA and total RNA samples were noted that were not corrected by chip scaling. Furthermore, each dataset (i.e., polyA$^+$ RNA and total RNA) showed similar differential gene expression between the respective groups of patients and controls. For example, the initial 11/11 dataset identified a larger than expected number of interferon-regulated genes. A gene-by-gene scaling approach thus was employed so that the two datasets could be combined and examined together. The scaling strategy was based on the assumption that the mean expression level (mean AD) of genes between the two control groups (total vs. polyA$^+$ RNA) should be equal. For each gene, the mean of the two control groups was compared to generate the gene-specific scaling factor. The polyA$^+$ samples were corrected by the scaling factor so that the means of the two control groups (total and polyA$^+$) were identical. This scaled dataset then was used for all subsequent analysis.

Identification of stress response genes: During the course of collecting and analyzing the various samples, it was determined that many genes in peripheral blood cells undergo striking stress responses following incubation ex vivo, even during somewhat limited periods of time (i.e., less than 1 hour). A formal experiment was designed and performed to identify those genes that were regulated by incubation of cells ex vivo. Changes in global gene expression were examined using whole blood after overnight shipment by a commercial carrier. This study utilized samples from eight healthy control individuals. Approximately 30 mL of blood was drawn into four CPT tubes. PBMCs were isolated from two tubes and resuspended in RNAlater (Ambion, Austin, Tex.). RNAlater immediately lyses the cells and protects the RNA from degradation, thus providing an accurate profile of gene expression immediately ex vivo. The RNA preserved in RNAlater and the two CPT tubes with whole blood were shipped by overnight carrier. Total RNA was extracted and prepared for hybridization as described above. Thus, global gene expression profiles were obtained from both a fresh blood sample and from blood shipped overnight, with both samples coming from the same blood draw.

Data were analyzed using MAS 4.0 and each chip was scaled to 1500. Absent and low expression values were assigned a threshold of 20 AD units as described above. A paired T-Test was used to compare the gene expression profiles of fresh blood vs. blood shipped by overnight carrier. Based on this experiment, 2076 genes were identified that displayed significant changes in expression under these environmental stresses ($p<0.01$). These genes, many of which are involved in various cell stress pathways, were excluded from further analysis due to the high level of variability that they exhibited.

Comparison analyses: The individual gene expression levels of SLE patients and controls were compared using an unpaired Student's T-test. Genes selected for further analysis met the following three criteria:

(i) p<0.001 by unpaired T-test,
(ii) change in expression of at least 1.5-fold when comparing the means of the two groups, and
(iii) difference in expression of at least 100 when comparing the means of the two groups.

Overall, 484 genes were differentially expressed at the p<0.001 level, while 178 genes were both differentially expressed at the p<0.001 level and showed mean AD values that differed by more than 1.5-fold. The final dataset of 161 individual genes (represented by 171 Genbank accession numbers) met all three criteria. These genes, which demonstrated differential expression between SLE patients and normal controls, are listed in Table 1.

Expression values for each of the 161 genes were converted to "fold-differences" by dividing each value by the mean of the control expression values. Unsupervised hierarchical clustering then was applied to the dataset. Hierarchical clustering was performed using Cluster and visualized using TreeView (M. Eisen, Stanford; available on the internet at rana.lbl.gov). This analysis identified gene expression patterns that differentiated most SLE patients from healthy controls. Thirty-seven of the 48 SLE patients clustered tightly together, while 11 of the patients co-clustered with controls. Six of the 42 control subjects clustered together with the large group of patients.

Most (124 of 161, 77%) of the genes that best distinguished SLE from control PBMCs were expressed at higher levels in SLE patients than in normal subjects. These are presented in Table 2. A number of these genes have known or suspected roles in the immune system. For example, many SLE patients were found to overexpress mRNA for the following cell surface markers: TNFR6 (Fas/CD95), a death receptor; ICAM-1 (CD54), an adhesion molecule; CD69, an activation antigen; and complement receptor 1. Of interest, three different Fc receptors were expressed at elevated levels: the Fc receptor for IgA (FCAR, CD89), and the IgG receptors FcRγIIA (CD32) and FcRγI (CD64). Three molecules in the inflammatory IL-1 cytokine pathway—IL-1β, the IL-1 receptor II (IL-1RII), and the IL-1 receptor antagonist—also were generally overexpressed. Interestingly, Jagged 1, a ligand for Notch 1 located in the SLE susceptibility interval on chromosome 20p, also was overexpressed in some patients. Other notable genes that were overexpressed in SLE patients include the signaling molecules MAP3K-8, RAB27, interleukin-6 signal transducer, the transcription factors v-ets 2, MADS box transcription factor 2, and the estrogen responsive zinc finger protein 147.

A number of genes were expressed at lower levels in patients than controls. These are presented in Table 3, and included T cell genes such as Lck, TCR delta, and TCR beta. Flow cytometry of freshly stained PBMCs was used to confirm that there was a T cell lymphopenia in many of the patients (i.e., about a 20% decrease, on average, in percentage of CD3$^+$ T cells). The patients also demonstrated a significant increase in the percentage of monocytes, as compared to the percentage of monocytes in controls. Specifically, PBMC populations from SLE patients (n=18) contained 52% T cells, 5% B cells, 28% monocytes/macrophages, and 15% NK cells. PMBC populations from control subjects (n=28) contained 65% T cells, 6% B cells, 13% monocytes/macrophages, and 16% NK cells. The percentages of T cells (p=0.014) and monocytes (p=0.00001) thus differed between SLE and controls. These differences in baseline cell populations clearly contribute to some of the differences in gene expression observed, and highlight the importance of documenting cell percentages in mixed cell populations.

Identification of IFN-regulated genes: One of the most striking mRNA clusters contained several genes previously identified as being interferon-regulated (Der et al. (1998) *Proc. Natl. Acad. Sci. U.S.A.* 95:15623). Interferons are highly active cytokines important for maintaining viral immunity (IFN-α and IFN-β) and for mediating TH1 immune responses (IFN-γ). Genes in this cluster were up-regulated in about half of the SLE patients, and were expressed at low levels in most of the control subjects.

Experiments were conducted to examine the extent to which the genes in this cluster could be regulated in PBMCs by IFN treatment in vitro. Peripheral blood was drawn from each of four healthy control individuals. PBMCs were isolated over Lymphocyte Separation Medium (Mediatech Cellgro, Herndon, Va.) according to the manufacturer's protocol. After the last wash, cells were resuspended in complete media (RPMI1640, 10% heat inactivated FBS, 2 mM L-glutamine, pen/strep) at a final concentration of $2 \times 10^6$ cells/mL. PBMCs were cultured for six hours at 37° C. with the following additions:

(i) PBS+0.1% BSA control,
(ii) IFN-α and IFN-β (R&D Systems, Minneapolis, Minn.), each at 1000 U/mL in PBS+0.1% BSA, and
(iii) IFN-γ (R&D Systems, Minneapolis, Minn.), 1000 U/mL in PBS+0.1%.

Following the incubation, total RNA was isolated, and cRNA probes were prepared for chip hybridization. Data were analyzed in MAS 4.0, and all chips were scaled to 1500. Absent and low expression values were assigned a threshold of 20 AD units as described above. Genes that met both of the criteria below in all four experiments were identified as IFN-regulated:

(i) change in expression of at least 2-fold when compared to untreated control, and
(ii) difference in expression of at least 500 AD units when compared to untreated control.

Changes in gene expression following IFN treatment were assessed relative to a six-hour control culture. This analysis identified 286 genes that demonstrated more than a 2-fold change in expression from baseline, and an absolute mean difference in the level of expression of greater than 500 units. The induction of many known IFN-regulated genes, such as Stat1, myxovirus resistance 1 (Mx-1), and ISGF-3, validated the approach. Using this list of IFN-regulated genes, 13 of 14 unique genes in the cluster were identified as bonafide IFN-regulated transcripts. Overall, 23 of the 161 genes (14.3%) were found to be IFN-regulated, compared with 7 genes (4.3%) that would have been expected by chance alone. The overrepresentation of interferon-regulated genes in the list of transcripts that best discriminated SLE patients from controls was consistently observed when a variety of different filters were used to define both IFN-regulated and SLE genes.

The mRNA levels of the IFNs themselves were not significantly different between patients and controls. Plasma/serum IFN-γ and IFN-α proteins were measured by ELISA (Pierce Endogen, Rockford, Ill.). IFN-γ was undetectable in all samples (less than 25 pg/mL). IFN-α was detectable in only two patients (26 and 29 pg/mL) and one control subject (56 pg/mL).

Figure 1:
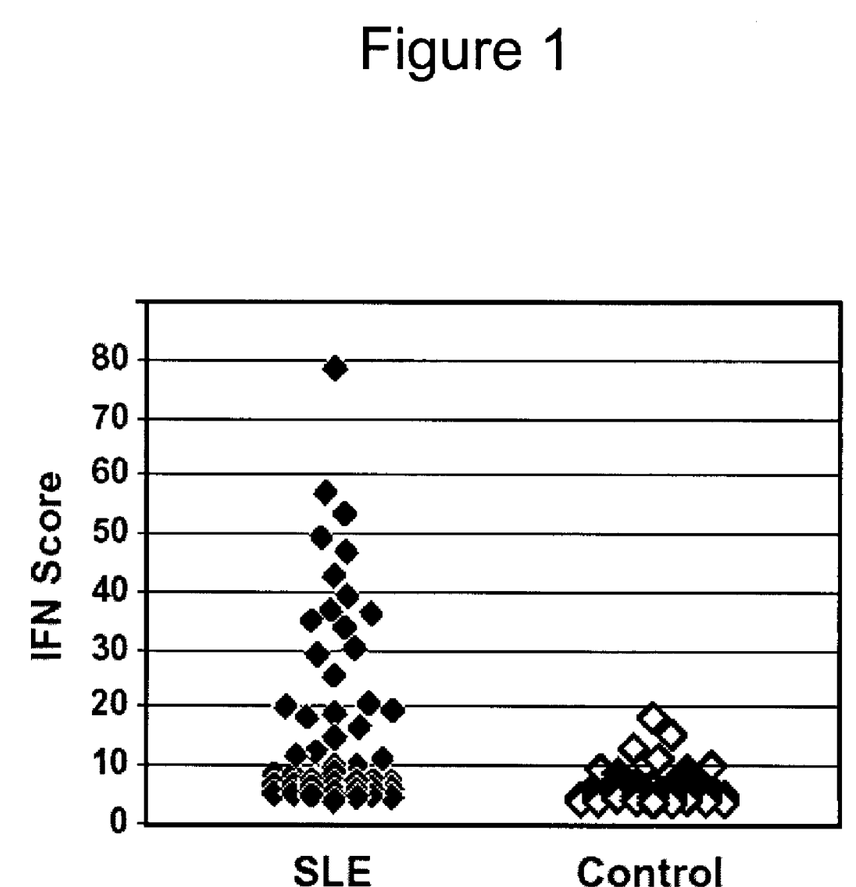
FIG. 1 is a graph plotting the IFN scores that were calculated for SLE patients and control subjects using the normalized expression levels of the 14 IFN-regulated genes that comprise the IFN signature; $p=2.8\times10^{-7}$.

An IFN "score" was calculated for each patient and control, based on expression of genes in the IFN cluster. Scores were calculated by first normalizing the expression values within each row of genes so that the maximum value in any row was 1.0. Then the columns (samples) were summed to obtain the score. The IFN score (mean±SD) for patients was 3.7±2.6, compared to controls 1.5±0.5, p=4.2×10$^{-7}$. Approximately half of the SLE patients exhibited an elevated IFN score, while the others had scores indistinguishable from controls (FIG. 1).

The lupus patient population was divided into two groups, with the IFN-high group containing the 24 patients with the highest IFN scores, and the IFN-low group containing the 24 patients with the lowest scores. Differences in gene expression were examined. Table 4 contains a list of the genes that displayed differential expression between the IFN-high and IFN-low groups. All of the genes listed in Table 4 were expressed at a greater level in the IFN-high group that in the IFN-low group.

Figure 2:
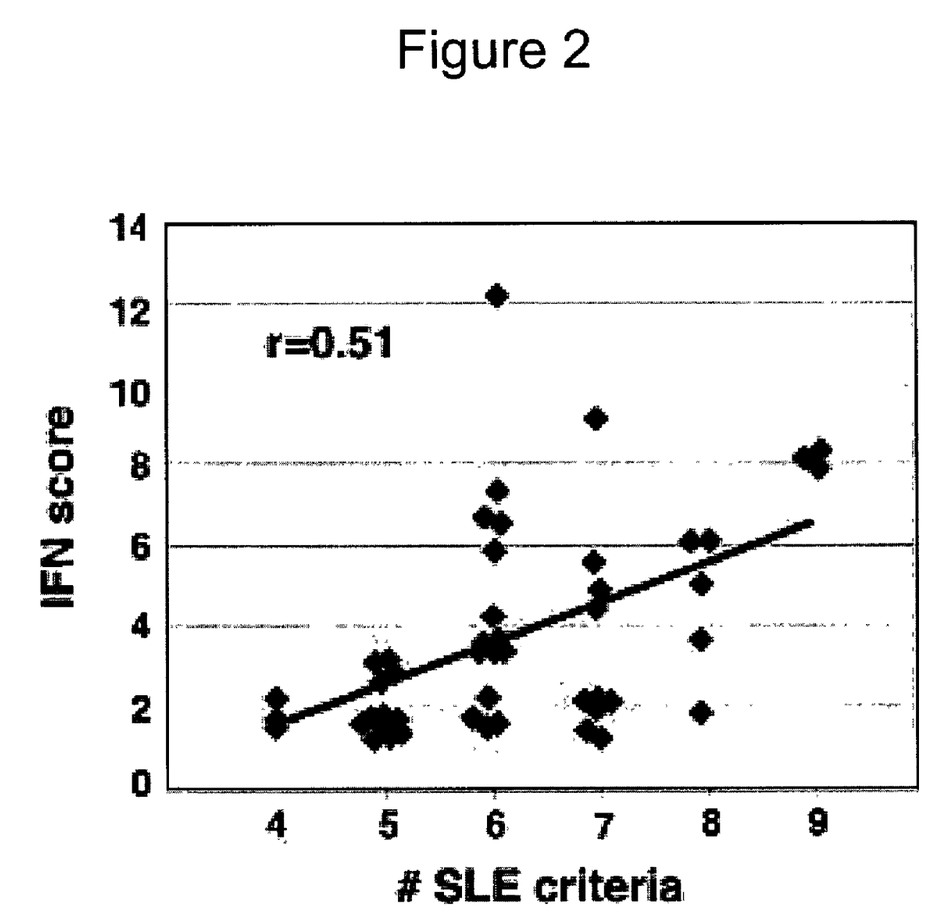
FIG. 2 is a graph plotting the number of SLE critieria observed in the 24 SLE patients with the highest IFN scores and in the 24 SLE patients with the lowest IFN scores; $p=0.002$.

Studies then were conducted to determine whether the IFN gene expression signature correlated with clinical features of SLE. SLE typically is diagnosed using eleven criteria developed by the ACR (Hochberg (1997) *Arthritis Rheum*. 40:1725). These criteria span the clinical spectrum of SLE and include skin criteria (malar rash, oral ulcers, photosensitivity, and discoid rash), systemic criteria (pleuritis or pericarditis, arthritis, renal disease, or CNS involvement), and laboratory criteria (cytopenias, anti-dsDNA or anti-phospholipid Abs, and antinuclear antibodies). A patient must meet four of these criteria to be classified as having definite SLE. The number of SLE criteria met by each patient was plotted against his or her IFN score (FIG. 2). This analysis revealed that the IFN score was correlated with the number of SLE criteria displayed in each patient.

Figure 3:
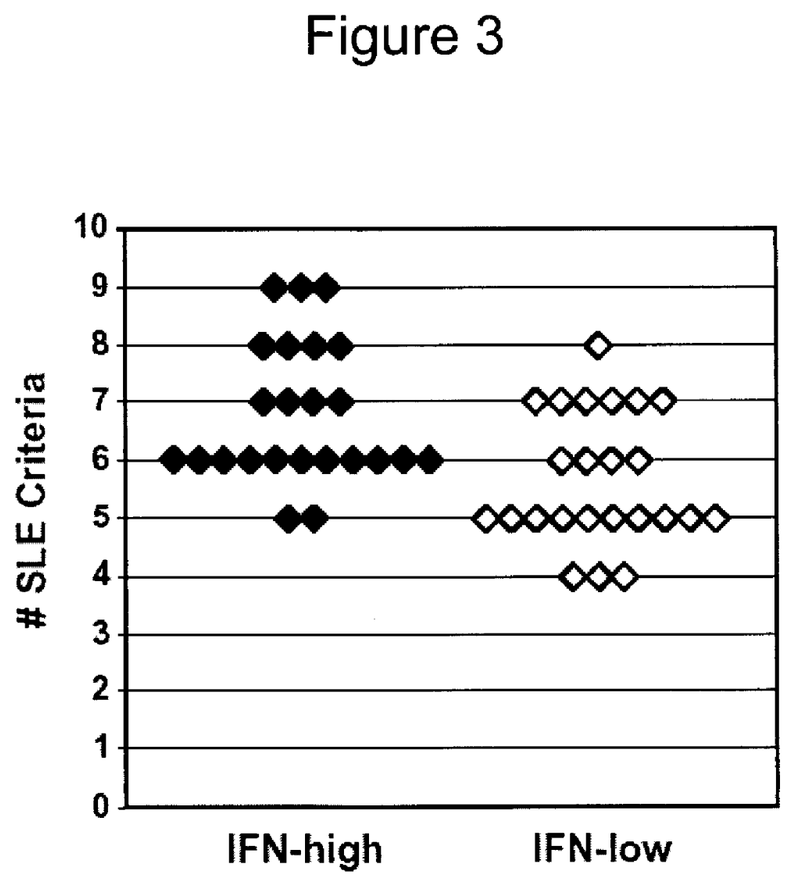
FIG. 3 is a graph plotting the number of SLE criteria met by each patient against the IFN score of each patient.
Figure 4:
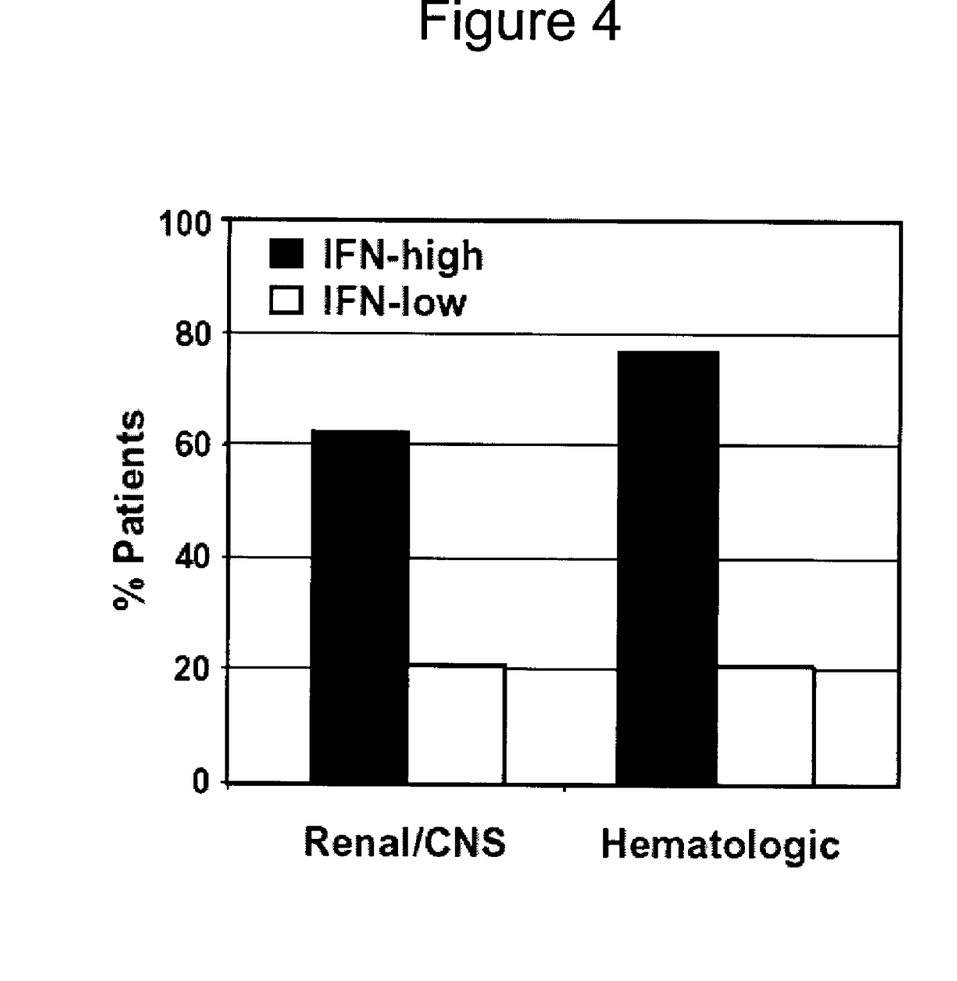
FIG. 4 is a bar graph showing the percent of patients in the IFN-high and IFN-low groups with ACR-defined criteria for renal and/or CNS disease ($p=7.7\times10^{-6}$) or hematologic involvement ($p=6.1\times10^{-9}$).

In a similar analysis, the clinical features of the 24 SLE patients with the highest IFN scores (IFN-high) were compared to the clinical features of the 24 SLE patients with the lowest scores (IFN-low). As depicted in FIG. 3, patients in the IFN-high group had a significantly higher number of SLE criteria (6.8±1.3) than those in the IFN-low group (5.7±1.1; p=0.004). Patients in the IFN-high group also showed a trend towards being diagnosed with SLE at an earlier age (25±12 compared with 30±13 years; p=0.192). Importantly, 15 of 24 patients (63%) in the IFN-high group fulfilled the ACR criteria for involvement of kidneys and/or the CNS, the most serious complications of lupus, compared with 5 of 24 patients (21%) in the IFN-low group (FIG. 4). In addition, 18 of 24 IFN-high patients (75%) showed hematologic involvement in their disease (severe leukopenia, hemolytic anemia or thrombocytopenia), compared with only 5 of 24 IFN-low patients (21%). An elevated interferon score thus correlated with the more severe manifestations of SLE.

The hypothesis that IFNs are important in the pathogenesis of lupus is supported by a number of observations. Mice transgenic for IFN-γ develop lupus-like autoimmunity (Seery et al. (1997) *J. Exp. Med.* 186:1451), and lupus-prone NZB/NZW F1 mice treated with anti-IFN-γ Abs or bred onto the IFN-γ$^{-/-}$ background show amelioration of disease (Jacob et al. (1987) *J. Exp. Med.* 166:798; and Balomenos et al. (1998) *J. Clin. Invest.* 101:364). The interferon-inducible gene IFI-202 has been identified as an SLE gene within the Nba2 SLE locus on mouse chromosome 1, NZB mice, the parental strain for this locus, show constitutively high expression of this transcription factor (Rozzo et al. (2001) *Immunity* 15:435). In humans, elevated levels of IFN-α have been reported in the sera of some SLE patients (for review see Ronnblom and Alm (2001) *J. Exp. Med.* 194:59), and a significant percentage of individuals treated with IFN-α for viral hepatitis develop lupus-related autoantibodies (Fukuyama et al. (2000) *Am. J. Gastroenterol.* 95:310). Finally, IFN-α in the sera of some pediatric SLE patients induces maturation of monocytes into highly active antigen-presenting plasmacytoid dendritic cells (Blanco et al. (2001) *Science* 294:1540).

While genes in IFN-signaling pathways exhibited dysregulated expression in some lupus patients, the mRNA levels of the IFNs themselves were not significantly different between patients and controls. IFN-γ protein was not detectable by ELISA in any patient or control sample, and IFN-α was detectable in only 2 of 48 patients and 1 of 42 controls. Thus, other cytokines that utilize Jak/Stat signaling pathways downstream of their receptors, such as IL-4, IL-13, or IL-2 (Hirano et al. (2000) *Oncogene* 19:2548), could contribute to the gene expression patterns observed.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for diagnosing severe systemic lupus erythematosus, said method comprising:
   (a) determining whether or not a human contains blood cells that express C1-inhibitor and lectin, galactoside-binding, soluble, 3 binding protein genes to an extent greater than the average level of expression exhibited in control blood cells from one or more control humans, and
   (b) diagnosing said human as having severe systemic lupus erythematosus if said human contains said blood cells and diagnosing said human as not having severe systemic lupus erythematosus if said human does not contain said blood cells.

2. The method of claim 1, wherein said one or more control humans are healthy humans.

3. The method of claim 1, wherein said one or more control humans are humans with mild systemic lupus erythematosus.

4. The method of claim 1, wherein said extent is greater than the average level of expression exhibited in control blood cells from at least 10 control humans.

5. The method of claim 1, wherein said extent is less than the average level of expression exhibited in control blood cells from at least 20 control humans.

6. The method of claim 1, wherein said determining step comprises measuring the level of mRNA expressed from said at least 2 of said genes.

* * * * *

UNITED STATES PATENT AND TRADEMARK OFFICE
CERTIFICATE OF CORRECTION

PATENT NO. : 7,118,865 B2
APPLICATION NO. : 10/222202
DATED : October 10, 2006
INVENTOR(S) : Timothy W. Behrens, Emily C. Baechler and Peter K. Gregersen It is certified that error appears in the above-identified patent and that said Letters Patent is hereby corrected as shown below:

Column 20, line 54, please delete "less" and insert --greater--therefor;

Column 20, line 59, please delete "at least 2 of said".

Signed and Sealed this

Sixth Day of February, 2007

JON W. DUDAS
*Director of the United States Patent and Trademark Office*